US00PP15795P2

(12) United States Plant Patent
Evison et al.

(10) Patent No.: US PP15,795 P2
(45) Date of Patent: Jun. 14, 2005

(54) ***CLEMATIS* VARIETY 'EVIPO014'**

(50) Latin Name: *Clematis viticella*
Varietal Denomination: EVIpo014

(75) Inventors: Raymond Evison, St. Sampson (GB); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/440,078

(22) Filed: May 15, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a tall growth habit, profuse, white flowers, and continuous summer flowering. The variety successfully propagates from softwood cuttings and is suitable for cultivation in commercial glasshouses. This new and distinct variety has shown to be uniform and stable in the resulting generations from propagation.

1 Drawing Sheet

Botanical Classification: Genus: *Clematis*. Species: *viticella*.

SUMMARY OF THE INVENTION/DISCOVERY

The present discovery constitutes a new and distinct variety of *Clematis* which originated from a chance seedling. 'EVIpo014' was discovered in a cultivated area. The variety resulted from a chance seedling.

The main characteristic that distinguishes 'EVIpo014' from the seed parent variety is that the unnamed seed parent has a Violet Blue flower color. The same of 'EVIpo014' is White Group 155A. The objective of the cultivation of this *Clematis* variety for commercial glasshouse and nursery culture was to create a new and distinct variety with:

1. Non-clinging habit;
2. Nodding, campanulate white flowers;
3. Suitability for garden situations;
4. Winter hardiness in zones 3 to 9;
5. Summer flowering.

These qualities required improvement in *Clematis* varieties that were in commercial cultivation and the objectives have been substantially achieved in the new variety, as evidenced by the unique combination of characteristics that are present in 'EVIpo014' which distinguish it from all other varieties of which we are aware.

The seeds were germinated and evaluations were conducted of the resulting *Clematis* plants in a controlled environment.

'EVIpo014' was selected by Raymond J. Evison and Mogens N. Olesen in their *Clematis* development program in Domarie Vineries Les Sauvagees, St. Sampsons, Guernsey, Channel Islands, United Kingdom in July, 1998.

Asexual reproduction of 'EVIpo014' by cuttings was first done by Raymond J. Evison and Mogens N. Olesen in Domarie Vineries Les Sauvagees, St. Sampsons, Guernsey, Channel Islands, United Kingdom in July 1998. This initial and subsequent propagations have demonstrated that the characteristics of 'EVIpo014' are true to type and are transmitted from one generation to the next.

BRIEF DESCRIPTION OF THE DRAWING

The accompanying color illustration show as true as is reasonably possible to obtain in color photographs of this type:

1. Bloom, upper side;
2. Bloom, lower side;
3. Stem, leaves, bud at ¼ opening, bud closed;
4. Stem and leaves;
5. Stem and juvenile foliage.

DETAILED DESCRIPTION OF THE VARIETY

The following is a detailed description of 'EVIpo014', as observed in its growth throughout the flowering period in glasshouses at Domarie Vineries Les Sauvagees, St. Sampsons, Guernsey, Channel Islands, United Kingdom. Observed plants are 2 years of age, and were cultivated in 2 liter pots. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing *Clematis* variety is integrifolia 'Alba', non-patented. Chart 1 details several physical characteristics of 'EVIpo014' and the comparison variety.

CHART 1

| | 'EVIpo14' | 'Alba' |
|---|---|---|
| Height | 1.5 to 2.0 m | 0.6 to 1.0 m |
| Flower color | White Group 155A. | White Group 155A, with intonations of Violet-Blue Group 91D. |

Parents: An unnamed seedling×an unnamed seedling.

FLOWER AND FLOWER BUD

Blooming habit: Recurrent, in late May, June, July, August and September.

Flower bud:
*Size.*—15 to 20 mm in length.
*Bud form.*—Ovoid.
*Bud diameter.*—10 to 12 mm.
*Bud length.*—15 to 20 mm.
*Bud color.*—Green Group 141D; Green Group 141D at ¼ opening.
*Tepals.*—White Group 155A.
*Peduncle.*—Surface: Smooth. Length: 120 to 180 mm. Color: Green Group 141A. Strength: Nodding.
*Receptacle.*—None.
*Borne.*—Compound dichasial cymes.

Flower bloom:
*Size.*—60 to 80 mm in diameter.
*Form.*—Campanulate, with tepals slightly reflexing.
*Depth.*—30 to 40 mm.
*Color.*—Upon opening, the upper tepal surface is White Group 155A. Upon opening, the lower tepal is White Group 155A. After opening, the upper tepal surface is White Group 155A. After opening, the lower tepal surface is White Group 155A. The base of the tepals is White Group 155A. The general tonality is white.
*Variations.*—On opening the lower tepal can show occasional tones of Yellow-Green Group 154D.
*Fragrance.*—None.
*Bloom duration.*—On the plant, 7 to 10 days. As a cut flower, 2 to 4 days.

Tepals:
*Tepal count.*—Single. Average range: 4.
*Shape.*—Elliptic. Apex: Acute to apiculate. Base: Rounded.
*Length.*—40 to 50 mm (if straightened).
*Width.*—20 mm.
*Margin.*—Entire.
*Cross section.*—Varies from straight to cupped along tepal length.
*Recurvature of tip.*—Strongly recurved, with a slight twist.
*Persistence.*—Tepals drop off cleanly.
*Arrangement.*—Tepals are arranged regularly.

Reproductive organs:
*Pollen.*—Quantity: Scant. Color: Yellow-White Group 158B.
*Anthers.*—Size: 3 to 5 mm long. Color: Yellow Group 13C.
*Arrangement.*—Regular.
*Filaments.*—Color: Yellow Group 19D.
*Styles.*—Color: Green Group 136D and Yellow Group 11D.
*Pistil.*—Quantity: 40 to 60.
*Seed.*—Quantity: 30 to 40 per seed head. Size: Medium. Shape: Circular to tear shaped. Diameter: 4 to 5 mm. Depth: 2 mm. Color: Green Group 143C, ripening to Greyed-Orange Group 166C.

PLANT

Plant form: Upright.
Plant growth: Moderately vigorous.
Height: Seasons growth attains 1.5 to 2 meters.
Spread: 0.5 M.
Hardiness: Trials to date show the variety hardy in USDA Zones 3–9.

Stems:
*Color.*—Young wood: Green Group 137C, with intonations of Purple Group 79B and Greyed-Orange Group 170A. Older wood: Greyed-Orange Group 165C.
*Internodes.*—Cross-section: Cylindrical. Length: 90 mm.
*Petioles.*—Size: Average length: 0 to 50 mm on compound leaf; length on simple leaf is 5 to 30 mm. Diameter is 1 mm. Color: Green Group 137C. Clasping: None.
*Bark.*—Young wood: Smooth. Older wood: Smooth.

Plant foliage: Deciduous. Simple leaves or compound, elliptic leaves consisting of 7 elliptic leaflets.
*Leaf size.*—Average compound leaf size is 80 to 100 mm (l)×50 to 60 mm (w). Terminal leaflet size is about 40 mm (l)×15 to 20 mm (w).
*Abundance.*—Average.
*Color of mature growth.*—Top: Medium-dark green. Green Group 137A. Bottom: Medium green. Green Group 137C.

Plant leaves and leaflets:
*Stipules.*—Absent.
*Petiole.*—Length: 0 to 50 mm. Underneath: Without prickles. Color: Green Group 137B.
*Leaflet shape.*—Elliptical with a rounded base and acute tip.
*Leaflet edge.*—Terminal leaflet margin is entire.
*Shape.*—Base of leaflet: Acute. Apex of leaflet: Acute.
*Texture.*—Upper side: Glabrous. Lower side: Veined.
*Thickness.*—Thin.
*Glossiness.*—Matte Finish.

Disease resistance: Subject to any disease that normally attacks the species, however the variety is more tolerant to Botrytis and *Clematis* Wilt than some *Clematis* known to us.

It is claimed:

1. A new and distinct variety of *Clematis* plant named 'Evipo014', as illustrated and described herein as a distinct and novel *clematis* variety due to its abundant white flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

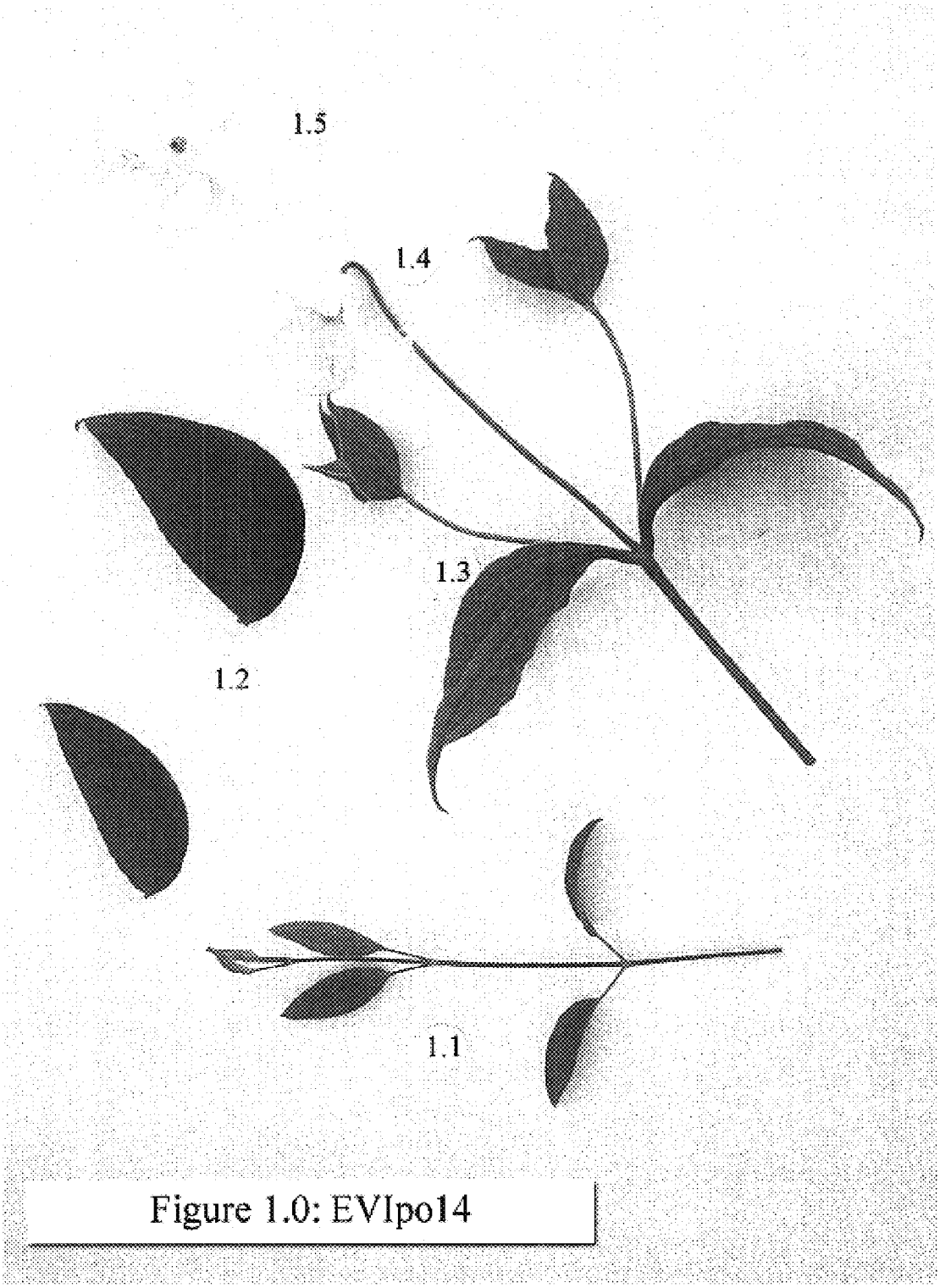
Figure 1.0: EVIpo14